United States Patent [19]

Cherukuri et al.

[11] Patent Number: 5,284,659
[45] Date of Patent: Feb. 8, 1994

[54] ENCAPSULATED FLAVOR WITH BIOADHESIVE CHARACTER IN PRESSED MINTS AND CONFECTIONS

[76] Inventors: Subraman R. Cherukuri, 10 Jean Dr., Towaco, N.J. 07082; Krishna P. Raman, 5 Marre Dr., Randolph, N.J. 07869; Gul Mansukhani, 97 Petrus Ave., Staten Island, N.Y. 10312; Angel M. Orama, 19 Elizabeth Ave., Stanhope, N.J. 07874

[21] Appl. No.: 502,464

[22] Filed: Mar. 30, 1990

[51] Int. Cl.⁵ ............................ A61K 9/20; A61K 9/28
[52] U.S. Cl. ................................... 424/441; 424/435; 424/439; 424/465; 424/468; 424/471; 424/472; 424/473; 424/484; 424/485; 424/486; 424/488; 424/487
[58] Field of Search ............... 424/441, 499, 435, 439, 424/472, 471, 473

[56] References Cited

U.S. PATENT DOCUMENTS

| | | | |
|---|---|---|---|
| 3,911,099 | 10/1975 | De Foney et al. | 424/435 |
| 4,292,299 | 9/1981 | Suzuki et al. | 424/472 |
| 4,778,676 | 10/1988 | Yang | 424/441 |
| 4,847,090 | 7/1989 | Della Posta et al. | 424/441 |
| 4,857,331 | 8/1989 | Shaw | 424/441 |
| 4,876,092 | 10/1989 | Mizobuchi et al. | 424/435 |
| 4,900,552 | 2/1990 | Sanvordeker et al. | 424/435 |
| 4,915,948 | 4/1990 | Gallopo | 424/499 |
| 5,032,406 | 7/1991 | Dansereau et al. | 424/471 |
| 5,059,416 | 10/1991 | Cherukuri et al. | 424/439 |
| 5,091,184 | 2/1992 | Khanna | 424/435 |

Primary Examiner—Thurman K. Page
Assistant Examiner—James M. Spear

[57] ABSTRACT

A confectionery compressed tablet designed to dissolve in the oral cavity and containing a flavor ingredient intimately bound with a bioadhesive is disclosed. The flavor and bioadhesive composition provide a unique mouthfeel so that as the confection dissolves in the oral cavity, a coating of flavor adheres to the moist areas of the oral cavity. There is also provided a confectionery compressed tablet characterized by a single product body with discrete phases contained therein which act to provide timed release of at least one flavor ingredient sequentially. A flavor and bioadhesive mixture can be prepared with a hydrophilic delivery system providing rapid initial delivery of the flavor and unique mouthfeel or as a part of a hydrophobic delivery system providing extended periods of flavor delivery and unique mouthfeel. There is also provided a process for preparing confectionery compressed tablets containing the unique flavor delivery system and mouthfeel.

24 Claims, 4 Drawing Sheets

ENCAPSULATED FLAVOR WITH BIOADHESIVE CHARACTER IN PRESSED MINTS AND CONFECTIONS

BACKGROUND OF THE INVENTION

The present invention relates to confections which are intended to reside in the oral cavity for a period of time while being consumed. In particular, the present invention provides among other things, confectionery tablets with both instant and timed delivery to the oral cavity of taste-affecting ingredients such as flavors, sweeteners, and mixtures thereof in compressed tablets.

Flavor delivery systems are well known in the art and may be divided into various classes based upon their physical characteristics, namely, liquid, emulsion, paste, or solid. Not only are these characteristics different, but also the potential uses for each type of flavor and method of manufacture differ as well.

In the past, considerable effort has been directed toward the preparation of flavoring materials. Specifically, flavor materials have been sought to provide greater intensity coupled with sustained flavor release for long periods of time.

To overcome difficulty with flavor oils in particular, various attempts have been made to encapsulate flavor oils or use dried ingredients to prolong the delivery of the flavors. Further, considerable effort has been directed to the development of delayed-release agents which will delay release of the flavor and permit uniform-release of the flavor over an extended period of time.

Spray drying is one of the most widely used techniques for encapsulating or fixing a flavor and such are well in the art. Flavor fixation has also been obtained by the extrusion method wherein the flavor oil is co-extruded with a water-soluble sugar or sugar mixture, dried and ground for use. These products find application in dry mixes for the instant release of the flavor upon contact with water. Such products generally contain 10% to 15% by weight of flavor oil. An extensive discussion of the prior art with respect to the extension of flavor is found in commonly/-assigned co-pending U.S. patent application having Ser. No. 07/463050, and U.S. patent application having Ser. No. 07/450756, both of which are incorporated by reference herein. These commonly assigned applications disclose methods and compositions for providing confectionery compressed tablets having both rapid initial delivery of a flavor ingredient and timed delivery of the same or of a second flavor ingredient over a period of time. The use of these flavor delivery systems provide improved confections capable of delivering both an initial rapid delivery as well as prolonged delivery of a flavor ingredient. While the aforementioned flavor delivery systems represent a dramatic improvement in flavor delivery, the present invention provides an alternative solution to the problem of flavor delivery.

In recent years, the adhesive properties of water soluble polymers have been explored as delivery systems for bio-effecting agents. Polymers, such as polyacrylic acid and hydroxypropylmethyl cellulose, for example, have been explored to provide delivery systems adhering to buccal, cervical, gastrointestinal, nasal and ocular mucosa as an administration route. The polymers are engineered to provide predetermined amounts of bio-effecting agents while at the same time anchor the dosage form on a selected mucous membrane.

The buccal route, which relies upon the mucous membranes of the oral cavity, has often been relied upon for administration of bio-effecting agents which are susceptible to inactivation by gastrointestinal enzymes and/or the hepatic "first pass" effect, i.e., inactivation of drugs during the first passage through the liver. Buccal administration is also useful for delivery of bio-effecting agents such as nitroglycerin which has a short duration of bioactivity.

It is, therefore, an object of the present invention to provide a multiple phase compressed tablet providing both a rapid initial delivery as well as timed delivery of flavor ingredients to the oral cavity.

It is another object of the present invention to provide a compressed tablet which has a bioadhesive contained therein to assist in delivery of flavor ingredients to the oral cavity.

It is a further object of the present invention to provide a compressed tablet which can be used to provide heightened as well as varied organoleptic responses which are pleasing to the consumer.

It is a still further object of the present invention to provide a compressed tablet containing flavor ingredients therein and which adheres to the oral mucosa while in the oral cavity.

SUMMARY OF THE INVENTION

In accordance with the present invention, there is provided a compressed tablet having a unique bioadhesive mouthfeel provided by tablets which adhere to the moist areas of the oral cavity and provide timed delivery of flavor ingredients thereto. The present invention may include a first phase which provides a physical structure for the tablet, and a second phase providing timed delivery of a flavor ingredient over a period of time. The first, the second or both phases may contain a bioadhesive which allows the confection to adhere to the oral mucosa and tongue in the oral cavity.

Alternatively, there is provided a compressed tablet having a flavor intimately bound with a bioadhesive to provide a confection having a unique mouthfeel of flavor adhering to the moist areas of the oral cavity. In this embodiment, the flavor and bioadhesive can be included as part of a hydrophilic system providing rapid initial delivery of the flavor and the organoleptic mouthfeel. Alternatively, the flavor and bioadhesive can be included as part of a hydrophobic system providing timed delivery of the flavor and extended periods of adherence of the flavor to the moist areas of the oral cavity.

The compressed tablets of the present invention include a first flavor ingredient intimately bound in a hydrophilic composition for instantaneous delivery of the first ingredient to the oral cavity. The first flavor ingredient is included in either the first phase, the second phase, or both first and second phases. Suitable hydrophilic compositions may be selected from the group consisting of polymer systems, gums, gelatin, starches, modified starches and other film formers. The flavors bound thereto can be present in an amount of from about 1% to about 30% by weight of the total hydrophilic composition.

The present invention also includes second flavor ingredient encapsulated in a hydrophobic composition along with a bioadhesive to provide timed delivery of the second ingredient to the oral cavity as well as adhesion of the confectionery tablet to the moist areas of the oral cavity. This encapsulated flavor ingredient can be included in either the first phase, the second phase, or both the first and second phases so that selected flavor-delivery sequences can be provided.

The hydrophobic component may be selected from fats, waxes, resins and mixtures thereof which are suitable for spray congealing the flavor ingredient together with a bioadhesive agent and is typically present in an amount of from about 0.5% to about 30% by weight.

The bioadhesive agent may be selected from, for example, methylcelluloses, acrylates and gums and can be included in the component in an amount of from about 0.5% to about 30% by weight of the total hydrophobic composition. A flavor is also present in an amount of from about 3% to about 30% by weight of the hydrophobic composition.

The invention also relates to a process for preparing confectionery compressed tablets having two phases and capable of adhering to the moist areas of the oral cavity to provide timed flavor release. The method includes preparing a first flavor ingredient and a second flavor ingredient and then preparing the first structural phase, including one or both of the flavor ingredients therein, followed by preparing the second phase containing a bioadhesive and including therein either one or both of the flavor ingredients. The phases are combined together to form a compressed tablet. In one preferred embodiment, the confectionery tablet is in a core-shell configuration in which the shell portion is a hard candy texture and structure and includes at least the hydrophilic flavor components so that it provides an initial burst of high intensity flavor in the oral cavity. In this preferred embodiment, the shell portion may or may not also include a small portion of the hydrophilic/bioadhesive spray-congealed flavor composition. In this way, the shell portion will sustain a continual high level of flavor in the oral cavity regardless of what is contained in the core portion. Similarly, the inclusion of bioadhesive containing compositions within the shell portion will initiate adherence of the confection to the moist areas of the oral cavity. The shell portion may also optionally include a breath deodorant such as copper gluconate.

In the same preferred embodiment, the core portion preferably includes at least the hydrophobically encapsulated bioadhesive flavor composition and is preferably of a softer texture. The outer shell portion can be preferably formed by compressing half of the tablet with the cavity formed therein followed by depositing a preformed second phase containing the bioadhesive in the cavity and forming thereover the other half of the shell portion and thereafter compressing the tablet to form the product of the present invention.

The hydrophilic composition containing the first flavor ingredient may be prepared by spray drying techniques or extrusion techniques which are known in the art.

The encapsulated second flavor ingredient contained within the bioadhesive/hydrophobic composition may be prepared by first heating the fat, wax or mixture thereof to its melting point and thereafter maintaining a temperature of about 65°-75° C. under agitation. An emulsifier may be added to the resulting melt, and in the instance where the delivery system is prepared to include a sweetener, the sweetener is likewise added thereto.

To the above mixture, the bioadhesive material such as a polymer or gum is added into the melted hydrophobic composition under agitation to provide a dispersion of the bioadhesive within the hydrophobic composition.

Before the flavor and hydrophobic/bioadhesive component are combined, an anticaking agent such as silicon dioxide is added to the flavor and mixed to form a slurry. The slurry is then added to the hydrophobic/bioadhesive component and the resulting composite is agitated until a first homogenous mixture is formed.

Emulsified flavor oil can then be added to the melted hydrophobic/bioadhesive component and is agitated to form a homogenous mixture which is thereafter sprayed congealed to form solid particles.

As a result of the present invention, confectionery compressed tablets may be provided which have not only an initial burst of flavor but also coat the moist areas of the oral cavity with a sustained high intensity release of flavor over a period of time by adhesion of the flavor component to the mucosal surfaces of the oral cavity and remaining thereon for extended periods of time.

Another advantage of the present invention is the ability to provide confections having a unique mouthfeel. Initially, the shell portion may impart a typical mouthfeel, however, as the confection dissolves in the oral cavity, the bioadhesive tendencies become more apparent providing prolonged sensation of the flavors within the oral cavity.

The aspect of the invention having separate phases allows a compressed tablet to be composed of ingredients which might otherwise interact with each other and thus not be suitable for delivery in the same confectionery unit. It is thus possible to prepare a compressed tablet which incorporated normally interactive flavor substances and keeps them substantially separated until the compressed tablet is placed in the oral cavity where it will be dissolved and the flavor ingredients released as intended for the users benefit.

The present invention includes both sugar-containing and sugarless confectionery compressed tablets, the size and weight of the piece depending upon the intended product. Usually, such tablets tend to weigh in the range of from about 1.5 to about 1.8 grams.

For a better understanding of the present invention, together with other and further objects, reference is made to the following description, taken in conjunction with the accompanying drawings, and its scope will be pointed out in the appended claims.

DETAILED DESCRIPTION OF THE INVENTION

Figure 1:
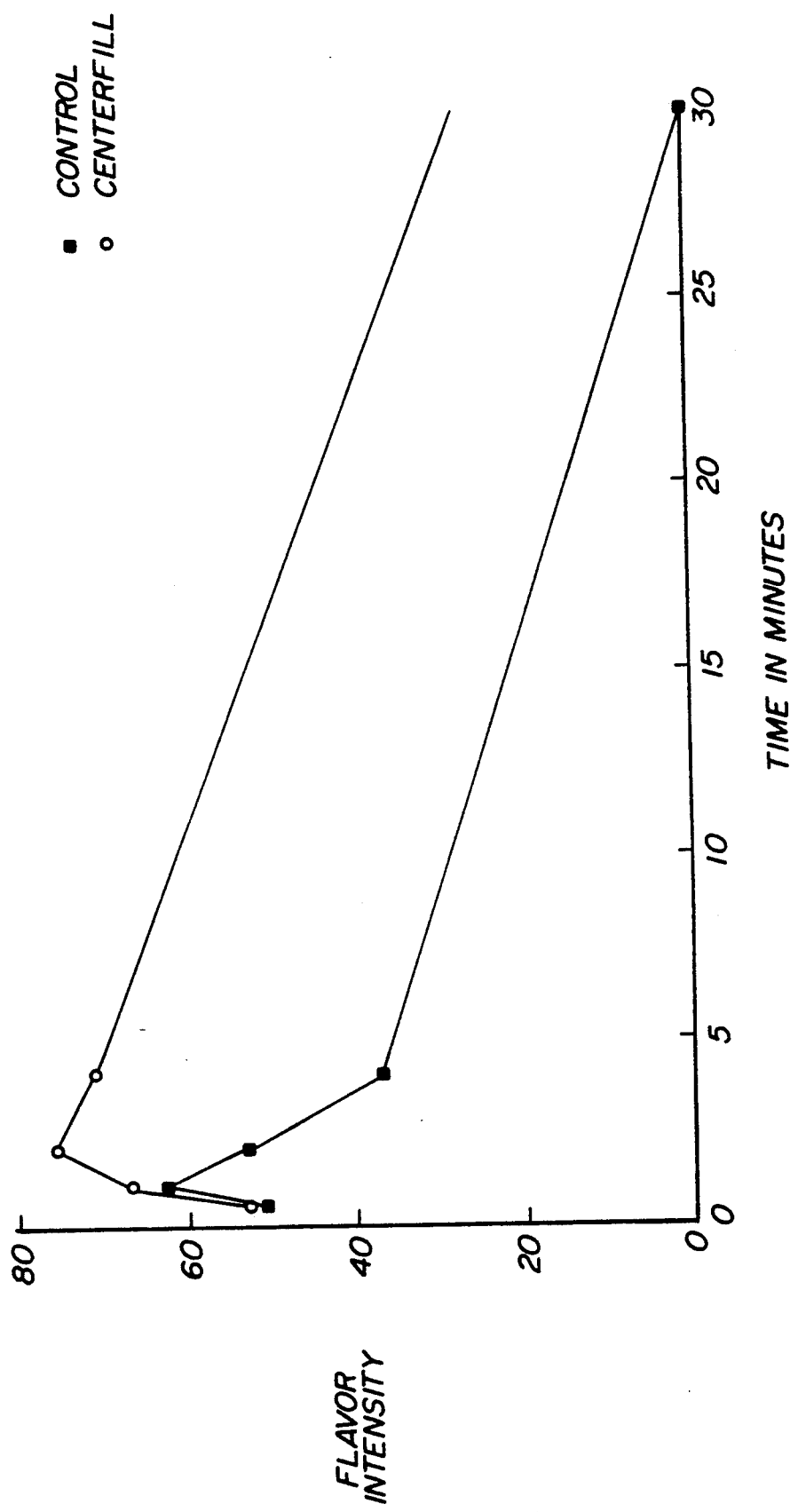
FIG. 1 is a graph presenting the results of comparative sensory evaluation testing of a peppermint flavored confectionery compressed tablet containing the inventive flavor delivery system and a control confectionery compressed tablet containing conventional liquid peppermint flavor.
Figure 2:
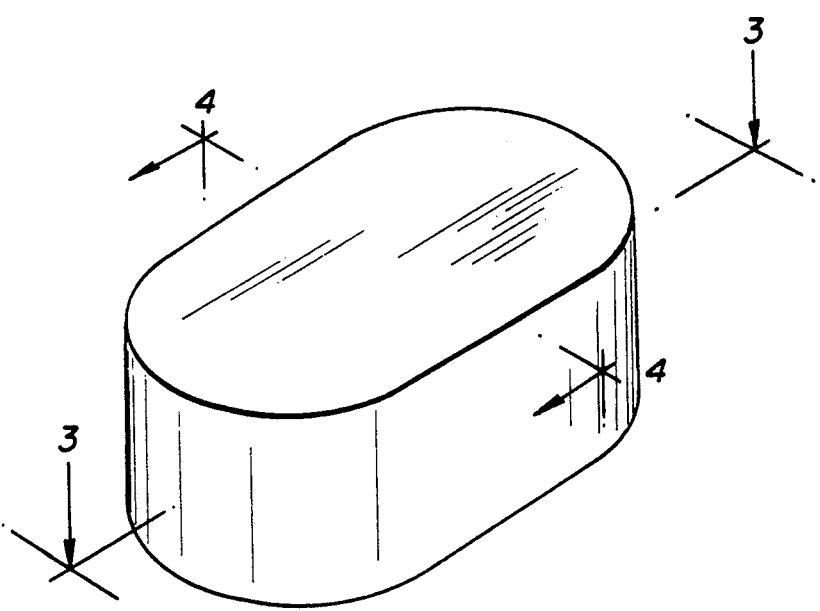
FIG. 2 is a perspective view of a confectionery compressed tablet made in accordance with a preferred embodiment of the present invention.

In accordance with the present invention, a confectionery compressed tablet having flavor ingredients combined therein, providing controlled release thereof and unique mouthfeel using bioadhesives is disclosed. The controlled release of the flavor ingredients contained within the tablets is achieved by providing a compressed tablet with at least two physical phases. A sequential flavor delivery system achieved by the differing physical phases offers improved release capabilities for the flavor ingredients. In this embodiment the bioadhesive properties of at least the second phase provide long lasting flavor release with a unique coating film of flavor on the moist areas of the oral cavity and teeth.

The present invention is concerned with a new and highly useful form of confections which provide the user with a unique bioadhesive mouthfeel and organoleptic satisfaction.

The compressed tablet may accordingly include:

(a) a first flavor ingredient present in an amount from about 0.1% to 0.5% by weight of a hydrophilic composition with which it is intimately bound to provide instantaneous delivery of the active ingredient; and (b) a second flavor ingredient present in an amount of from about 3% to 30% by weight of a hydrophobic encapsulating composition containing a bioadhesive so as to provide delivery of the second flavor ingredient over a period of time while both the tablet and encapsulated flavors adhere to the moist areas of the oral cavity.

Overall, the confectionery compressed tablet includes flavor components in an amount of from about 0.1% to about 0.5% by weight of the total weight of the tablet.

Alternatively, a single flavor can be included with a bioadhesive in a confectionery compressed tablet to provide a product having either the properties of hydrophilic delivery systems providing rapid initial delivery of the flavor and mouthfeel or alternatively combined with a hydrophobic delivery system providing extended periods of flavor release and the unique mouthfeel.

Useful flavoring agents may be chosen from synthetic flavoring liquids such as synthetic flavor oils and flavoring aromatics and/or oils; and/or liquids, oleoresin or extracts derived from plants, leaves, flowers, fruits, etc., and combinations thereof. Preferably, the flavor component is selected from spearmint oil, cinnamon oil, oil of wintergreen (methylsalicylate) and peppermint oil, clove oil, bay oil, anise oil, eucalyptus oil, thyme oil, cedar leaf oil, oil of nutmeg, allspice, oil of sage, mace, oil of bitter almonds, and cassia oil. Also useful are artificial, natural or synthetic flavors including fruit flavors such as vanilla, and citrus oils including lemon, orange, grape, lime and grapefruit and fruit essences including apple, pear, peach, grape, strawberry, raspberry, cherry, plum, pineapple, apricot and so forth.

Suitable auxiliary flavorings including both natural and artificial flavors, and mints such as peppermint, menthol, artificial vanilla, cinnamon, various fruit flavors, both individual and mixed, and the like are contemplated. Such flavorings are generally utilized in amounts that will vary depending upon the amount of the flavor encapsulation delivery system employed and may, for example, range in amounts of up to about 10% by weight of the final compressed tablet composition weight. Thus the auxiliary flavorings may be present in the encapsulated flavor delivery system, and, optionally, in the compressed tablet composition itself.

The hydrophilic composition to which the first flavor ingredient is bound may be selected from compounds suitable for inclusion in spray drying procedures and techniques which are well known in the art.

For example, the hydrophilic composition may be prepared by spray drying techniques which are well known in the art. In this procedure, a flavor oil is usually blended with a film forming agent dispersed in water and then emulsified to form a stable emulsion. Emulsification is necessary because flavor oils are insoluble in the water needed to dissolve the film forming agent. Maintaining low inlet temperatures (i.e, around 155° C.) as well as minimizing the residence time in the dryer are beneficial if the flavor is chemically unstable. Air drying conditions depend on the emulsion and product characteristics such as particle size of the product required. Modifications to the use of heat to remove the water from the emulsion have also been attempted. Some of these include the use of a dehydrating solvent as the drying medium rather than hot air. Freeze drying has also been contemplated.

A non-limiting list of suitable hydrophilic compounds includes polymer systems, gums, gelatin, starches, modified starches and other film formers. Gums can be selected from the group consisting of gum arabic, xanthan gum, agar, alginate (sodium), carrageenan, guar, karaya, locust bean, tragacanth, ghatto, cellulose ethers including, among others, Methocel ™ and Ethocel ™ (products provided by Dow Chemical Company), also acrylates such as Carbopol ®.

The flavor ingredient is intimately bound thereto and can be present in an amount of from about 0.1% to about 0.5% by weight of the total hydrophilic composition. The hydrophilic composition, in turn, makes up from about 82% to about 99+% of the compressed tablet by weight. Preferably, the hydrophilic composition accounts for between about 86% to about 96% and most preferably from about 90% to about 94% of the compressed tablet.

The hydrophobic composition to which the second flavor ingredient and bioadhesive are encapsulated is preferably prepared by spray congealing the flavor and bioadhesive with a hydrophobic material. Examples of suitable hydrophobic materials include fats, waxes, resins and mixtures thereof. In a preferred embodiment, the hydrophobic composition provides a texturally different mouthfeel than the hydrophilic composition. For example, the hydrophobic composition may be softer and more pliable than the hydrophilic composition.

The hydrophobic composition may make up from about 0.1% to about 18% of the compressed tablet by weight. Preferably, the hydrophobic composition accounts for between about 4% to about 14% and most preferably from about 6% to about 10% by weight.

Bioadhesives are those compounds which adhere to moist areas of biological membranes and range from slight adherence to practically permanent affixing. For purposes of the present invention, bioadhesives mean those compounds suitable for placement in the oral cavity. Although bioadhesives have been used for delivery of bio-effecting agents, it has now been found that they significantly enhance flavor delivery for confections designed to reside in the oral cavity for a period of time while being consumed. When combined with flavors and spray congealed with a hydrophobic material such as a fat, wax or resin, it has been discovered that the timed delivery of flavor provided by hydrophobic encapsulation is enhanced by allowing the flavor to adhere to the moist areas of the oral cavity. The flavors continue to be released while at the same time provide a unique organoleptic experience. The tongue, teeth and mucous membranes are pleasantly coated with a long lasting flavor release composition.

Relatively, high adhesion is obtainable with, for example, compounds such as amylopectin, carboxymethylcellulose, sodium, hydroxyethylcellulose. Moderate levels of adhesion may be obtainable with, for example, acrylates, gelatins, guar gum, karaya gum and tragacanth. Lower levels of adhesion are provided by agar, alginic acid, carboxymethylcellulose, calcium, dextran, methylcellulose, pectin, polyethylene-glycol and polyvinylpyrrolidone.

The bioadhesive may be present in an amount of from about 0.5% to 30% by weight of the hydrophobic component. Preferably, the bioadhesive is present in an amount of from about 7% to about 25%, and most preferably from about 18% to about 22%.

As stated hereinabove, the second flavor ingredient and bioadhesive are typically encapsulated by spray congealing with hydrophobic materials such as fats, waxes, resins and mixtures thereof.

In addition to flavor ingredients, the bioadhesive may be encapsulated with a bio-effecting agent such as breath fresheners, breath deodorants, antigingivitis agents and combinations thereof. Suitable breath fresheners include, for example, alpha ionone, methyl ionone, menthol, licorice, rose oil, violet leaves, salicylates, cyclamen, jasmine oil, elemi oil, clove oil, cardamon oil, anise oil, myrrh resin and mixtures thereof. Suitable breath deodorants include, for example, copper gluconate. Antigingivitis agents include, for example, chlorhexidine, thymol, menthol, methyl salicylate, eucalyptol and mixtures thereof.

The process of spray congealing as used herein refers to feeding of the second homogenous mixture through a heat controlled spray nozzle, and the formation of atomized liquid droplet within a closed, temperature regulated chamber, so that the droplets cool and solidify upon contacting the cooler temperature of the surrounding atmosphere, which may, for example, be on the order of 25° C. The nozzle pressure is regulated to control particle droplet size, and droplets cool and congeal once they are emitted from the nozzle and contact the cooler environment. The result of this process is a dry particle or agglomerate which may have an approximate elliptical or spherical shape.

Suitable fats include fatty acids such as hydrogenated or partially hydrogenated oils, with representative materials comprising palm oil, palm kernel oil, soybean oil, cottonseed oil, peanut oil, rapeseed oil, rice bran oil, sunflower oil, safflower oil, and mixtures thereof. Other materials also useful as fats herein may be selected from monoglycerides, diglycerides, triglycerides, polyglycerol esters, sorbitol esters, and mixtures thereof. When the hydrophobic material is a fat alone, the fat is present in an amount of from about 50% to about 85% by weight of the hydrophobic composition. The remainder of the hydrophobic composition would include a flavor in an amount of from about 5% to about 30% by weight, a bioadhesive in an amount of from about 0.5% to about 30% as well as emulsifiers, diluents, and anticaking agents.

Suitable waxes include natural waxes, synthetic waxes, and mixtures thereof, and in particular, comprise materials selected from the group consisting of paraffin wax, beeswax, carnauba wax, candelilla wax, lanolin wax, bayberry wax, sugar cane wax, petrolatum, carbowax, spermaceti wax, rice bran wax, microcrystalline wax, and mixtures thereof. When the hydrophobic material is a wax alone, the wax is present in an amount of from about 45% to about 85%. In this embodiment, the remainder of the hydrophobic composition includes a flavor in an amount of from about 5% to about 30% and a bioadhesive in an amount of from about 0.5% to about 30%.

Suitable resins may be selected from pentaerythritol ester of partially hydrogenated wood rosin, pentaerythritol ester of wood rosin, glycerol ester of wood rosin, glycerol ester of partially dimerized rosin, glycerol ester of polymerized rosin, glycerol ester of tall oil rosin, glycerol ester of wood rosin and partially hydrogenated wood/gum rosin and partially hydrogenated methyl ester of rosin, such as polymers of alpha-pinene or beta-pinene; terpene rosins including polyterpene and mixtures thereof. When the hydrophobic material is a resin alone, the resin is present in an amount of from about 20% to about 80% by weight of the hydrophobic composition. The remainder of the hydrophobic composition contains flavor in an amount of from about 5% to about 30%, the bioadhesive is present in an amount of from about 0.5% to about 30%.

Naturally, the foregoing is illustrative and not restrictive of suitable hydrophobic materials. The above-mentioned hydrophobic material may be combined with each other and be present in substantially similar proportions.

The hydrophobic composition may optionally include an emulsifier in an amount of up to 10% by weight. In the instance where the emulsifiers are employed, suitable emulsifiers include mono-, di- and triglyceride esters of fatty acids, polyglycerol esters and the like. More particularly, the emulsifier may be selected from the group consisting of lecithin, stearates, ester derivatives of stearates, almitate, ester derivatives of palmitate, oleates, ester derivatives of oleates, glycerides, sucrose polyesters, polyglycerolesters, and mixtures thereof. In a preferred embodiment, the emulsifier component may be present in an amount from about 2% to about 7% by weight of the hydrophobic encapsulation composition. In another preferred embodiment, the emulsifier may be present in an amount from about 4% to about 6% by weight.

In accordance with a further embodiment, the hydrophobic composition of the present invention may be combined with a diluent, lubricant, and/or bonding agent. Such agents are well known in the art. For example, diluents may include lactose, avicel microcrystalline cellulose NF, or starch, talc, sorbitol, mannitol, polydextrose, calcium carbonate, Palatinit ®, maltitol, xylitol, other sugar alcohols and sugar. Lubricants, for example, include stearic acid or magnesium stearate. Polyethylene glycol is an example of a suitable bonding agent.

The present invention includes both sugar-containing and sugarless confectionery compressed tablets. A sweetener can also be added to one or both of the flavor compositions in an amount that may range up to about 30% by weight and preferably from about 12% to about 13% by weight of the encapsulation, to offer a combined sensation of flavor and sweetness. The present invention contemplates the inclusion of those sweeteners well known in the art, including both natural and artificial sweeteners.

Suitable sweeteners may be selected from the following non-limiting list: sugars such as sucrose, glucose (corn syrup), dextrose, invert sugar, fructose, and mixtures thereof, saccharine and its various salts such as the sodium or calcium salt; cyclamic acid and its various salts such as the sodium salt; the dipeptide sweeteners such as aspartame; dihydrochalcone compounds, glycyrrhizin; Stevia Rebaudiana (Stevioside); glycyrrhizin, dipotassium glycyrrhizin, phenylalanine 1-methyl ester (Aspartame); chloro derivatives of sucrose; dihydroflavinol; hydroxyguaiacol esters; L-amino dicarboxylic acid gem-diamines; L-aminodicarboxylic acid aminoalkenoic acid ester amides; and sugar alcohols such as sorbitol, sorbitol syrup, mannitol, xylitol, and the like. Also contemplated as an additional sweetener is the nonfermentable sugar substitute (hydrogenated starch hydrolysate) which is described in U.S. Pat. No. Re. 26,959. Also contemplated is the synthetic sweetener 3,6-dihydro-6-methyl1-1-1,2,3-oxathiazin-4-one-2,2-dioxide, particularly the potassium (acesulfame-K), sodium and calcium salts thereof as described in German Patent No. 2,001,017.7, 4,1,',6,-Trichloro-4,1',6'-trideoxygalactosucrose (Sucralose, a commercially available product of McNeil Specialty Products Company, Skillman, N.J.); L-alpha-Aspartyl-N-(2,2,4,4-tatramethyl-3-thietanyl)-D-alaninamide hydrate (Alitame, a commercially available product of Pfizer, New York, N.Y.); and thaumatin (Talin).

The above sweeteners and similar intense sweeteners not listed above often present special problems when they are included in ingestible products. For example, certain sweeteners present stability problems, such as Aspartame which breaks down into undesirable byproducts in the presence of aldehydes, ketones, moisture and the like. Similarly, other sweeteners exhibit a bitter aftertaste or off-note, such as Saccharin (a commercially available product of PMC Specialty Group Inc., Cincinnati, Ohio), Stevioside, Acesulfame-K, glycyrrhizin and its salts, and Talin. The incorporation of the aforenoted sweeteners into the present delivery system overcomes the prior drawbacks to their use, as the stability and taste-making capability of the present delivery system provides the necessary protection for these intense sweeteners and improves and enhances their sweetness sensation in ingestible products.

The confectionery compressed tablets of the present invention may also optionally include a colorant, present in an amount of from about 1% by weight to about 6% by weight. The colorants may include other dyes suitable for food, drug and cosmetic applications, and known as FD&C dyes and the like. The materials acceptable for the foregoing spectrum of use are preferably water-soluble. Illustrative examples include indigoid dye, known as FD&C Blue No. 2, which is the disodium salt of 5,5'-indigotindisulfonic acid. Similarly, the dye known as FD&C Green No. 1 comprises a triphenylmethane dye and is the monosodium salts of 4-[4-N-ethyl-p-sulfobenzylamino)diphenylmethylene]-[1-(N-ethyl-N-p-sulfoniumbenzyl)-2-5-cyclohexadieneimine]. A full recitation of all FD&C and D&C dyes and their corresponding chemical structures may be found in the Kirk-Othmer Encyclopedia of Chemical Technology, in Volume 5, pages 857–884, which is incorporated herein by reference.

With respect to confectionery compressed tablet formulations, such will contain a tablet granulation base and various additives, such as sweeteners and flavors. The tablet granulation base employed will vary depending on various factors such as the type of base used, friability desired and other components used to make this final product. The confectionery compressed tablet may additionally include the conventional additives of flavoring agents, coloring agents, emulsifiers and additional fillers. The variations that one may practice with regard to these confections are wide ranging and within the ability of those skilled in the art particularly with regard to the use of additional composition fillers, flavoring components, use of coloring agents, etc.

Ingredients which are sensitive to moisture and subject to deterioration in the presence of moisture, will particularly benefit from the present invention since they can be protected for extended periods of time. Furthermore, in the case of having a need to affect controlled release of a flavor and/or sweetener with an off-taste, the present invention is very effective since release can be directly related to necessary composition proportions. Thus, a flavor ingredient having, for example, a very bitter taste can be administered to an individual by simply providing a controlled release which is at such a low level that it does not adversely affect the perception by the consumer. A further use is to provide sustained release of a high-intensity sweetener at a very low concentration such that even without increasing the overall amount of the sweetener, for example, a confectionery compressed tablet composition can be sustained over a prolonged period of time.

A representative process for preparing a confectionery compressed tablet which includes the inventive long lasting flavor release with bioadhesive properties is as follows:

Initially, a first phase which is structurally supportive of the compressed tablet is prepared- A sweetener/bulking agent such as sugar or sorbitol is blended for a sufficient time, for example, five minutes, before adding a breath deodorant such as copper gluconate. Thereafter, mixing is continued for a time sufficient to effect dispersion of the ingredients, for example, about three minutes. A spray dried flavor such as peppermint, for example, is then added to the ingredients set forth above and blending is continued. It has been found that about three minutes of additional mixing time is sufficient to incorporate spray dried flavor. Thereafter, a coloring agent, if necessary, and lubricant are added and blended with the above-mentioned ingredients. For example, it has been found that coloring agents and lubricants are sufficiently dispersed in the mixture after blending for approximately two minutes.

Separately, at least a second phase which contains hydrophobically encapsulated flavor and bioadhesive is prepared. For example, using a fat as a source of hydrophobic encapsulation material, fats and an emulsifier are melted and maintained at a temperature of about 65° to 75° C. under agitation. Thereafter, a bioadhesive such as polymer/gum mixture is added to the melted fat under continuous agitation to effect sufficient dispersion. Separately, an anitcaking agent such as calcium phosphate, calcium stearate, magnesium silicate (talc) or silicon dioxide (Syloid ®) is added to a flavor oil and mixed to form a slurry. The slurry is thereafter added to the hydrophobic/bioadhesive mixture under agitation until a homogenous mixture is formed. The hot melt mix containing the fats, emulsifier, bioadhesive, anticaking agent, and flavor oil is thereafter spray congealed to form hydrophobically encapsulated flavor and bioadhesive. The encapsulated bioadhesive flavor is thereafter incorporated into the second phase as follows:

Optionally, a diluent may be blended with a lubricant for approximately ten minutes. Next, a bonding agent is added and mixed with the above ingredients for a time sufficient to effect dispersion, approximately two minutes. The hydrophobically encapsulated flavor and bioadhesive is then added and mixing is continued for approximately two minutes more to complete the preparation of the phase.

The separate phases are thereafter compressed separately in a tablet compression machine to provide the confectionery compressed tablets of the present invention.

In the case of a core-shell tablet, the core is compressed for placement in the shell portion. A first half of the shell portion is deposited and compressed in a tablet die. The previously-compressed core is placed thereon followed by a subsequent deposition of the remaining shell material thereover. The entire tablet composite is then compressed into a two phase product in accordance with the present invention.

Figure 3:
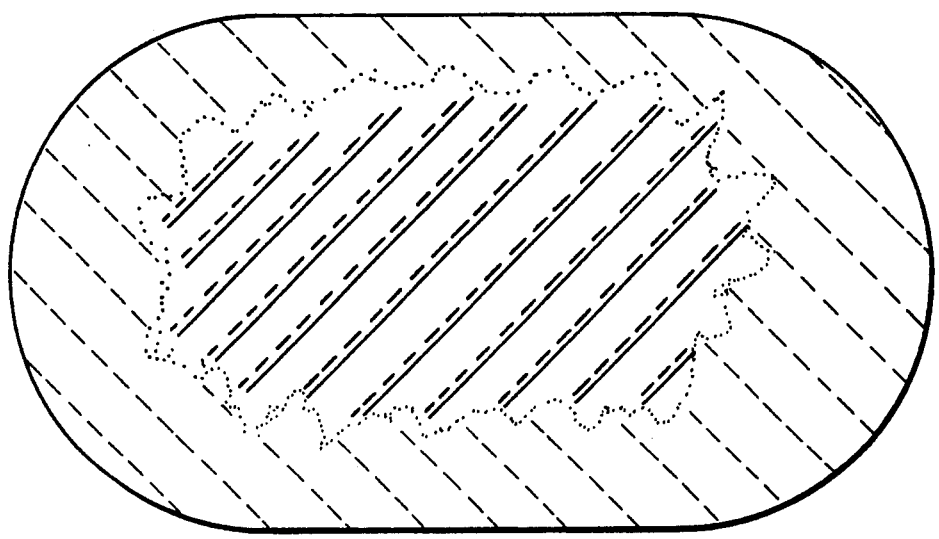
FIG. 3 is a cross-sectional view of the tablet taken along the line 3—3 of FIG. 2 showing a shell first phase substantially enveloping a core second phase.
Figure 4:
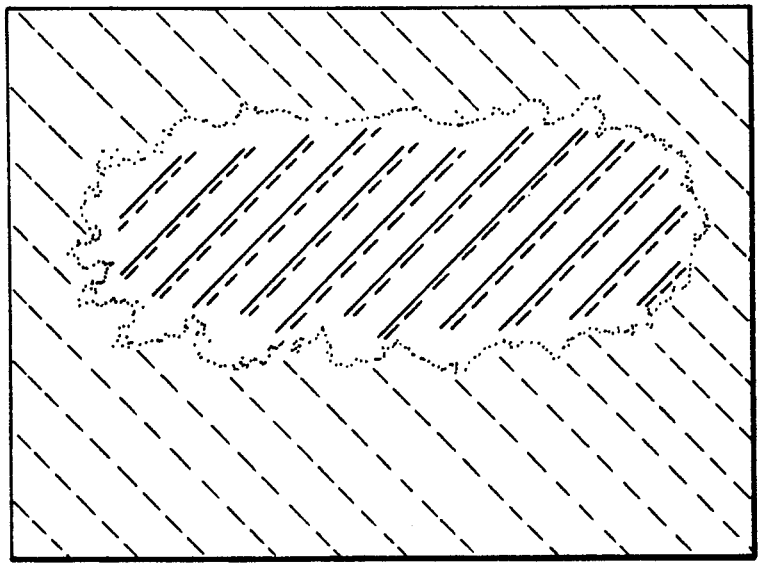
FIG. 4 is a cross-sectional view of the tablet hereof taken along line 4—4 of FIG. 2, showing a first phase substantially enveloping a second phase.
Figure 5:
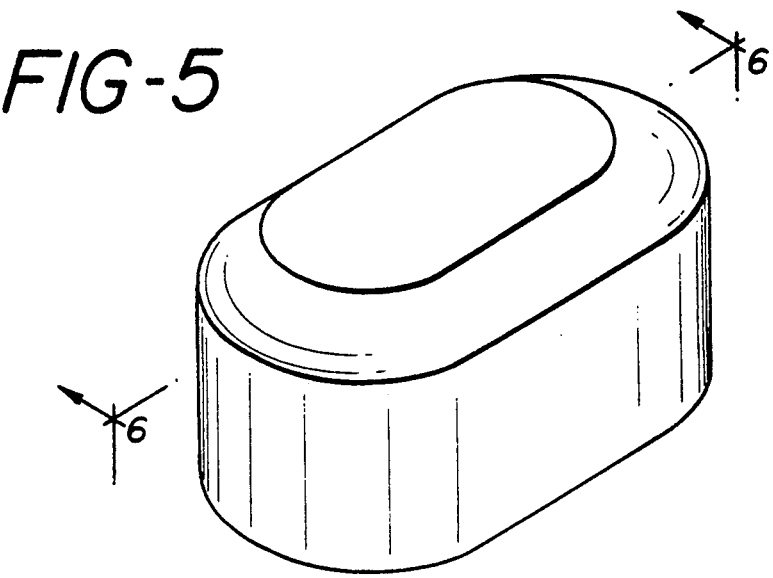
FIG. 5 is a perspective view of a confectionery compressed tablet prepared in accordance with a second embodiment of the invention.
Figure 6:
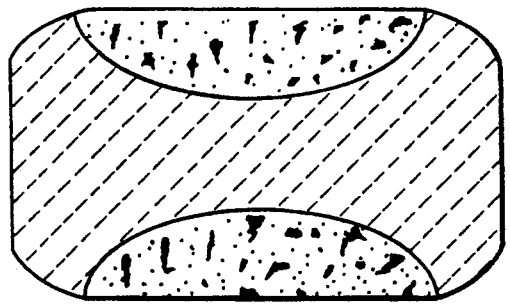
FIG. 6 is a cross-sectional view of the tablet shown in FIG. 5.

Referring now to FIGS. 3-5 an example of a possible embodiment of confectionery compressed tablets which can be made in accordance with the invention is shown. The common characteristic of such products is that they each comprise at least two discrete phases and the first phase is structurally supportive of a compressed tablet shape and substantially envelopes the second phase which is present as a core. The depicted forms all have a generally circular planar profile body shape, being, e.g., cylindrical, but it will be understood that other shapes are contemplated. FIG. 6 shows another embodiment of the present invention wherein the first phase is generally the middle and circumferential portion and the second phase has been fixed on either sides. The resulting tablet has a cross-section as shown in FIG. 6.

In addition to providing long lasting flavor release and unique flavor adhering properties, it will be seen that the present invention readily lends itself to employment in variations of colors and/or flavors in the separate phases of the compressed tablet. In a preferred embodiment, the compressed tablet releases two or more flavors by having a different flavor in the first phase being released initially, and a mint breath freshening flavor in the second phase adhering to the moist areas of the oral cavity, and released over a period of time.

The foregoing description is offered by way of illustration and in fulfillment of applicants' duty to disclose the best mode for the practice of the invention. Accordingly, the above procedures may be modified within the skill of the art, and all such modifications are contemplated herein and made a part hereof.

Tests were conducted using the confection of the present invention to compare it with confection products not containing the hydrophobically encapsulated flavor and bioadhesive, and it was found that not only were the flavor enhancing properties of the bioadhesive evident on the moist areas of the oral cavity, but also that such inventive confections were capable of delivering heightened levels of flavor for extended periods of time.

EXAMPLES

The following Examples serve to provide further appreciation of the invention but are not meant in any way to restrict the effective scope of the invention.

EXAMPLE I

A control confectionery compressed tablet was prepared using the following formulation.

| CONTROL SAMPLE | |
|---|---|
| INGREDIENT | PERCENT BY WEIGHT |
| Shell Component | |
| Sugar | 97.676 |
| Breath Deodorant | 0.748 |
| Lubricant | 0.234 |
| Flavor Beads | 1.280 |
| Liquid Flavor | 0.062 |
| | 100.00 |
| Core | |
| Fat Encapsulation | — |
| Diluent | — |
| | 0.0 |

Additionally, inventive confections with the novel hydrophobically encapsulated bioadhesive flavor were prepared in accordance with the following formula.

TABLE I

A representative fat encapsulation formula prepared in accordance with the present invention is as follows.

| FAT ENCAPSULATION | |
|---|---|
| INGREDIENT | PERCENT BY WEIGHT |
| Partially hydrogenated soybean oil (fat) | 48.00 |
| Glycerol Monostearate (Emulsifier) | 5.00 |
| Vegetable Oil Blend (Fat) | 10.00 |
| Anticaking Agent (Syloid) | 2.00 |
| Flavor Oil (Peppermint) | 15.00 |
| Hydroxyethylcellulose Viscosity 2000 (Bioadhesive) | 20.00 |
| | 100.00 |

TABLE II

| | INVENTIVE SAMPLES | | |
|---|---|---|---|
| | PERCENT BY WEIGHT | | |
| | Example I | Example II | Example III |
| INGREDIENT | | | |
| Shell Component | | | |
| Sugar | 97.676 | 97.676 | 97.676 |
| Breath Deodorant | 0.748 | 0.748 | 0.748 |
| Lubricant | 0.234 | 0.234 | 0.234 |
| Flavor Beads (8% Flavor) | 1.280 | 1.280 | 1.280 |
| Liquid Flavor | 0.062 | 0.062 | 0.062 |
| | 100.00 | 100.00 | 100.00 |
| Core | | | |
| Fat Encapsulation (15% flavor) | 100.00 | 59.88 | 40.32 |
| Diluent | — | 40.12 | 59.68 |
| | 100.00 | 100.00 | 100.00 |
| TABLET WEIGHT RATIO | | | |
| Shell/Core | 94/6 | 90/10 | 85/15 |

The above compositions were prepared in accordance with the method described hereinabove in the individual proportions as set forth in Table II. Confectionery compressed tablets with multiple encapsulation systems. The Control Sample and Inventive Example I were then subjected to testing for sensory evaluation. The results of the sensory evaluation are set forth in FIG. 1.

Referring to FIG. 1, the results of the evaluation demonstrate a significantly improved compressed tablet product. The inventive product demonstrated an initial flavor burst, and sustained flavor intensity. The high intensity of the initial burst exceeded that of the Control. Moreover, the longevity of flavor delivery at a high intensity as a result of the present invention was evident throughout the testing period of thirty minutes. Unlike the Control formulation which had no flavor intensity perception after thirty minutes, the inventive products were able to still provide significant flavor delivery for periods in excess of 60 minutes.

In addition to extended time periods of flavor delivery, the product of the present invention provided the user with a unique mouthfeel. As the confection containing the hydrophobically encapsulated flavor and bioadhesive released in the oral cavity, the user obtains a unique long lasting coating of hydrophobically encapsulated flavors. The hydrophobically encapsulated flavors dissolve slowly on all moist areas of the oral cavity and continue to deliver flavor at a high intensity for thirty minutes or more.

The compressed tablets made in accordance with the present invention which exhibit extenuated initial flavor burst, and heightened flavor intensity throughout the consumption period while the flavor oil adhere to the moist areas of the oral cavity can be refined and engineered to provide virtually any desired release pattern in the oral cavity. Such properties have been heretofore unobtainable in prior art compressed tablets. The unique bioadhesive properties of confections containing hydrophobically encapsulated flavors provide a unique mouthfeel. Also, heretofore unobtainable in prior art compressed tablets.

While there have been described what are presently believed to be the preferred embodiments of the present invention, those skilled in the art will realize that changes and modifications may be made thereto without departing from the spirit of the invention, and it is intended to claim all such changes and modifications as fall within the true scope of the invention.

What is claimed is:

1. A two phase system in a single compressed confection tablet for delivering at least one active ingredient in a timed release manner through the buccal route or through releasing a first ingredient into the oral cavity, wherein said phases define separate regions within said compressed confection tablet comprising:
   (a) at least 82% by weight of a hydrophilic component comprising a flavor and a matrix selected from the group consisting of: polymer systems, gums, gelatin, starches, modified starches and film forming compounds; and
   (b) up to 18% by weight of a separate hydrophobic component comprising:
   (i) said active ingredient;
   (ii) said first ingredient;
   (iii) a bioadhesive compound; and
   (iv) a hydrophobic encapsulation medium, wherein said first ingredient is selected from the group consisting of flavors, sweeteners and mixtures thereof.

2. The system of claim 1, wherein said flavor is selected from the group consisting of: spearmint oil, cinnamon oil, oil of wintergreen (methyl silicylate), peppermint oil, lemon oil, orange oil, grape oil, lime oil, grapefruit oil, apple essence, strawberry essence, cherry essence, pineapple essence, banana oil and mixtures thereof.

3. The system of claim 1, wherein said sweetener is selected from the group consisting of: amino acid-based sweeteners, dipeptide sweeteners, glycyrrhizin, saccharine and salts thereof, acesulfame salts, cyclamates, steviosides, talin, chloro-derivatives of sucrose, dihydrochalcone compounds and mixtures thereof.

4. The system of claim 1, wherein said bioadhesive compound is selected from the group consisting of: amylopectin, carboxymethylcelluloses, hydroxyethylcelluloses, acrylates, gelatin, guar gum, karaya gum, tragacanth, agar, alginic acid, dextran, methylcellulose, pectin, polyethylene glycol, polyvinylpyrrolidone and mixtures thereof.

5. The system of claim 1, wherein said bioadhesive compound comprises less than about 1% by weight of said system.

6. The system of claim 1, wherein said active ingredient comprises a bio-effecting agent.

7. The system of claim 1, wherein said bio-effecting agent is selected from the group consisting of: breath fresheners, breath deodorants, antigingivitis agents and mixtures thereof.

8. The system of claim 7, wherein said breath freshener is selected from the group consisting of alpha ionone, methyl ionone, menthol, licorice, rose oil, violet leaves, salicylates, cyclamen, jasmine oil, elemi oil, clove oil, cardamon oil, anise oil, myrrh resin and mixtures thereof.

9. The system of claim 7, wherein said breath deodorant is copper gluconate.

10. The system of claim 7, wherein said antigingivitis agent is selected from the group consisting of chlorhexidine, thymol, menthol, methyl salicylates, eucalyptol and mixtures thereof.

11. The system of claim 1, wherein said bioadhesive compound comprises between about 0.5% and about 30% by weight of said hydrophobic component.

12. The system of claim 1, wherein said bioadhesive compound comprises between about 7% to about 25% by weight of said hydrophobic component.

13. The system of claim 12, wherein said bioadhesive compound comprises between about 18% to about 22% by weight of said hydrophobic component.

14. The system of claim 1, wherein said hydrophilic component further comprises said active ingredient.

15. The system of claim 1, wherein said hydrophilic component further comprises a second active ingredient, whereby said second active ingredient is delivered for absorption through mucosa more rapidly than said first ingredient.

16. The system of claim 1, wherein said hydrophilic component is selected from the group consisting of polymers, gelatin, gum arabic, starches, modified starches, maltodextrin, corn syrup solids, hydrocolloids, carrageenan and acrylates.

17. The system of claim 1, wherein said hydrophilic component completely envelops said hydrophobic phase.

18. The system of claim 1, wherein said hydrophobic component comprises between about 0.1% and about 18% by weight of said tablet.

19. The system of claim 18, wherein said hydrophobic component comprises between about 4% and about 14% by weight of said system.

20. The system of claim 19, wherein said hydrophobic component comprises between about 6% and about 10% by weight of said system.

21. The system of claim 1, wherein said hydrophobic encapsulation medium is selected from the group consisting of fats, waxes, resins and mixtures thereof.

22. The system of claim 21, wherein said fat is selected from the group consisting of hydrogenated and partially hydrogenated oils.

23. The system of claim 21, wherein said fat is selected from the group consisting of monoglycerides, diglycerides, triglycerides, polyglycerol esters, sorbitol esters and mixtures thereof.

24. A method for preparing a two phase system in a single compressed confection tablet for delivering at least one active ingredient in a time release manner through the buccal route or through releasing a first ingredient into the oral cavity, wherein said phases define separate regions within said compressed confection tablet comprising the steps of:
  (a) preparing a hydrophilic component comprising a flavor and a matrix selected from the group consisting of polymer systems, gums, gelatin, starches, modified starches and film forming compounds;
  (b) separately preparing a separate hydrophobic component comprising:
    (i) said active ingredient;
    (ii) said first ingredient;
    (iii) a bioadhesive compound; and
    (iv) a hydrophobic encapsulation medium, wherein said first ingredient is selected from the group consisting of flavors, sweeteners and mixtures thereof; and
  (c) combining at least 82% by weight of said hydrophilic phase and up to 18% by weight of said hydrophobic phase to form a compressed confection tablet having separate regions for said hydrophilic phase and said hydrophobic phase.

* * * * *